United States Patent
Sato et al.

(10) Patent No.: US 12,369,582 B2
(45) Date of Patent: Jul. 29, 2025

(54) PYRIDYLOXYACETIC ACID COMPOUND AND USE OF SAME

(71) Applicant: SUMITOMO CHEMICAL COMPANY, LIMITED, Tokyo (JP)

(72) Inventors: Yuki Sato, Anpachi-gun (JP); Hiroaki Okamoto, Oita (JP); Yuta Honda, Takarazuka (JP); Kazuyasu Tani, Kurashiki (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 587 days.

(21) Appl. No.: 17/773,995

(22) PCT Filed: Nov. 9, 2020

(86) PCT No.: PCT/JP2020/041700
§ 371 (c)(1),
(2) Date: May 3, 2022

(87) PCT Pub. No.: WO2021/117394
PCT Pub. Date: Jun. 17, 2021

(65) Prior Publication Data
US 2022/0378045 A1    Dec. 1, 2022

(30) Foreign Application Priority Data
Dec. 11, 2019  (JP) ................. 2019-223480

(51) Int. Cl.
*A01N 43/40* (2006.01)
*C07D 213/69* (2006.01)

(52) U.S. Cl.
CPC ........... *A01N 43/40* (2013.01); *C07D 213/69* (2013.01)

(58) Field of Classification Search
CPC .............................. A01N 43/40; C07D 213/69
See application file for complete search history.

(56) References Cited

U.S. PATENT DOCUMENTS

| | | |
|---|---|---|
| 2019/0059374 A1 | 2/2019 | Pawlak, II et al. |
| 2019/0174762 A1 | 6/2019 | Yamada |
| 2019/0202787 A1 | 7/2019 | Yamada |
| 2019/0223435 A1 | 7/2019 | Yamada |

FOREIGN PATENT DOCUMENTS

| | | |
|---|---|---|
| WO | WO 2007/083090 A2 | 7/2007 |
| WO | WO 2018/038188 A1 | 3/2018 |
| WO | WO 2018/038189 A1 | 3/2018 |
| WO | WO 2018/038190 A1 | 3/2018 |
| WO | WO 2019/040699 A1 | 2/2019 |

OTHER PUBLICATIONS

International Search Report for PCT/JP2020/041700 mailed on Dec. 22, 2020.

*Primary Examiner* — Genevieve S Alley
(74) *Attorney, Agent, or Firm* — Birch, Stewart, Kolasch & Birch, LLP

(57) ABSTRACT

The present invention provides 2-{[3-(2-chloro-4-fluorophenoxy)pyridin-2-yl]oxy}acetic acid or an alkali metal salt thereof having an excellent control effect on plant diseases.

3 Claims, No Drawings

PYRIDYLOXYACETIC ACID COMPOUND AND USE OF SAME

TECHNICAL FIELD

The present invention relates to a pyridyloxyacetic acid compound and a use thereof.

BACKGROUND ART

Conventionally, various compounds have been developed for controlling plant diseases and put to practical use (see Non-Patent Document 1). Patent Document 1 describes 2-{[3-(2-chloro-4-fluorophenoxy)pyridin-2-yl]oxy}acetic acid ethyl ester (hereinafter, referred to as Compound B) as a production intermediate of a herbicide.

PRIOR ART DOCUMENTS

Patent Document

Patent Document 1: WO 2007/083090

Non-Patent Document

Non-Patent Document 1: The Pesticide Manual—17th edition (published by BCPC) ISBN 978-1-901396-88-1

SUMMARY OF THE INVENTION

Problems to be Solved by the Invention

An object of the present invention is to provide a compound having an excellent control effect on plant diseases.

Means for Solving the Problems

The present invention is as follows.
[1] 2-{[3-(2-Chloro-4-fluorophenoxy)pyridin-2-yl]oxy}acetic acid (hereinafter, referred to as Compound A) or an alkali metal salt thereof.
[2] A composition comprising the compound according to [1] or the alkali metal salt thereof and an inert carrier.
[3] A method for controlling a plant disease by treating a plant or soil with an effective amount of the compound according to [1] or the alkali metal salt thereof.

Effect of the Invention

According to the present invention, plant diseases can be controlled.

MODE FOR CARRYING OUT THE INVENTION

Examples of the alkali metal salt of Compound A include a lithium salt, potassium salt and sodium salt of Compound A. The alkali metal salt of Compound A may be a hydrate.

The composition of the present invention contains Compound A or the alkali metal salt thereof and an inert carrier. The composition of the present invention is usually formulated into an emulsion, an oil, a powder, a granule, a wettable powder, a water-dispersible granule, a flowable formulation, a dry flowable formulation, a microcapsule or the like by mixing Compound A or the alkali metal salt thereof with an inert carrier such as a solid carrier or a liquid carrier, and adding a surfactant and other auxiliaries, as necessary, for formulation.

The composition of the present invention usually contains 0.0001 to 95% by weight of Compound A or the alkali metal salt thereof.

Examples of the solid carrier used in the formulation include fine powders and granules of clays (kaolin clay, diatomaceous earth, bentonite, acid clay, and the like), dry silica, wet silica, talc, ceramics, other inorganic minerals (sericite, quartz, sulfur, activated carbon, calcium carbonate, and the like), chemical fertilizers (ammonium sulfate, ammonium phosphate, ammonium nitrate, urea, ammonium chloride, and the like), and the like, and synthetic resins (polyester resins such as polypropylene, polyacrylonitrile, polymethyl methacrylate, and polyethylene terephthalate, nylon resins such as nylon-6, nylon-11, and nylon-66, polyamide resins, polyvinyl chloride, polyvinylidene chloride, vinyl chloride-propylene copolymers, and the like).

Examples of the liquid carrier include water, alcohols (methanol, ethanol, and the like), ketones (acetone, methyl ethyl ketone, and the like), aromatic hydrocarbons (toluene, xylene, and the like), aliphatic hydrocarbons (hexane, cyclohexane, and the like), esters (ethyl acetate, butyl acetate, and the like), nitriles (acetonitrile and the like), ethers (diisopropyl ether, diethylene glycol dimethyl ether, and the like), amides (N,N-dimethylformamide, and the like), sulfoxides (dimethyl sulfoxide and the like), and vegetable oils (soybean oil, cottonseed oil, and the like).

Examples of the surfactant include nonionic surfactants such as polyoxyethylene alkyl ethers, polyoxyethylene alkyl aryl ethers, and polyethylene glycol fatty acid esters, and anionic surfactants such as alkyl sulfonates, alkyl benzene sulfonates, and alkyl sulfates.

Examples of other auxiliaries for formulation include fixing agents, dispersants, colorants, stabilizers, and the like, specifically, for example, casein, gelatin, saccharides (starch, gum arabic, cellulose derivatives, alginic acid, and the like), lignin derivatives, bentonite, synthetic water-soluble polymers (polyvinyl alcohol, polyvinyl pyrrolidone, polyacrylic acids, and the like), acidic isopropyl phosphate, 2,6-di-tert-butyl-4-methylphenol, and BHA (mixture of 2-tert-butyl-4-methoxyphenol and 3-tert-butyl-4-methoxyphenol).

Compound A or the alkali metal salt thereof has an effect on plant pathogenic bacteria. Examples of plant diseases derived from plant pathogenic bacteria include the following. The scientific name of the pathogenic bacteria causing the disease is shown in parenthesis.

Rice diseases: blast (*Pyricularia oryzae*), brown spot (*Cochliobolus miyabeanus*), sheath blight (*Rhizoctonia solani*), bakanae disease (*Gibberella fujikuroi*), downy mildew (*Sclerophthora macrospora*), false blast and head blight (*Epicoccum nigrum*), seedling blight (*Trichoderma viride, Rhizopus oryzae*);

Wheat diseases: powdery mildew (*Blumeria graminis*), Fusarium blight (*Fusarium graminearum, Fusarium avenaceum, Fusarium culmorum, Microdochium nivale*), stripe rust (*Puccinia striiformis*), stem rust (*Puccinia graminis*), leaf rust (*Puccinia recondita*), snow mold (*Microdochium nivale, Microdochium majus*), typhula snow blight (*Typhula incarnata, Typhula ishikariensis*), loose smut (*Ustilago tritici*), stinking smut (*Tilletia caries, Tilletia controversa*), eyespot (*Pseudocercosporella herpotrichoides*), leaf blotch (*Septoria tritici*), glume blotch (*Stagonospora nodorum*), tan spot (*Pyrenophora tritici-repentis*), rhizoctonia seeding blight (*Rhizoctonia solani*), take-all disease (*Gaeumannomyces graminis*), blast (*Pyricularia graminis-tritici*);

Barley diseases: powdery mildew (*Blumeria graminis*), Fusarium head blight (*Fusarium graminearum, Fusarium avenaceum, Fusarium culmorum, Microdochium nivale*), stripe rust (*Puccinia striiformis*), stem rust (*Puccinia graminis*), dwarf leaf rust (*Puccinia hordei*), loose smut (*Ustilago nuda*), scald (*Rhynchosporium secalis*), net blotch (*Pyrenophora teres*), spot blotch (*Cochliobolus sativus*), stripe (*Pyrenophora graminea*), Ramularia leaf spot (*Ramularia collocygni*), rhizoctonia seeding blight (*Rhizoctonia solani*);

Corn diseases: rust (*Puccinia sorghi*), southern rust (*Puccinia polysora*), northern leaf blight (*Setosphaeria turcica*), tropical rust (*Physopella zeae*), southern leaf blight (*Cochliobolus heterostrophus*), anthracnose (*Colletotrichum graminicola*), gray leaf spot (*Cercospora zeae-maydis*), eyespot (*Kabatiella zeae*), Phaeosphaeria leaf spot (*Phaeosphaeria maydis*), Diplodia rot (*Stenocarpella maydis, Stenocarpella macrospora*), stalk rot (*Fusarium graminearum, Fusarium verticilioides, Colletotrichum graminicola*), smut (*Ustilago maydis*), Physoderma disease (*Physoderma maydis*);

Cotton diseases: anthracnose (*Colletotrichum gossypii*), grey mildew (*Ramularia areola*), Alternaria leaf spot (*Alternaria macrospora, Alternaria gossypii*), black root rot (*Thielaviopsis basicola*);

Coffee diseases: rust (*Hemileia vastatrix*), leaf spot (*Cercospora coffeicola*);

Rapeseed diseases: Sclerotinia rot (*Sclerotinia sclerotiorum*), gray leaf spot (*Alternaria brassicae*), root rot (*Phoma lingam*), light leaf spot (*Pyrenopeziza brassicae*);

Sugarcane diseases: rust (*Puccinia melanocephela, Puccinia kuehnii*), smut (*Ustilago scitaminea*);

Sunflower diseases: rust (*Puccinia helianthi*), downy mildew (*Plasmopara halstedii*);

Citrus diseases: melanose (*Diaporthe citri*), scab (*Elsinoe fawcetti*), green mold (*Penicillium digitatum*), blue mold (*Penicillium italicum*), Phytophthora rot (*Phytophthora parasitica, Phytophthora citrophthora*), Aspergillus rot (*Aspergillus niger*);

Apple diseases: blossom blight (*Monilinia mali*), valsa canker (*Valsa ceratosperma*), powdery mildew (*Podosphaera leucotricha*), Alternaria leaf spot (*Alternaria alternata* apple pathotype), scab (*Venturia inaequalis*), bitter rot (*Glomerella cingulata, Colletotrichum acutatum*), blotch (*Diplocarpon mali*), ring rot (*Botryosphaeria berengeriana*), crown rot (*Phytophtora cactorum*), rust (*Gymnosporangium juniperi-virginianae, Gymnosporangium yamadae*);

Pear diseases: scab (*Venturia nashicola, Venturia pirina*), black spot (*Alternaria alternata* Japanese pear pathotype), rust (*Gymnosporangium haraeanum*);

Peach diseases: brown rot (*Monilinia fructicola*), scab (*Cladosporium carpophilum*), Phomopsis rot (*Phomopsis* sp.), leaf curl (*Taphrina deformans*);

Grape diseases: anthracnose (*Elsinoe ampelina*), ripe rot (*Glomerella cingulata, Colletotrichum acutatum*), powdery mildew (*Uncinula necator*), rust (*Phakopsora ampelopsidis*), black rot (*Guignardia bidwellii*), downy mildew (*Plasmopara viticola*);

Diseases of Japanese persimmon: anthracnose (*Gloeosporium kaki, Colletotrichum acutatum*), leaf spot (*Cercospora kaki, Mycosphaerella nawae*);

Diseases of gourd family: anthracnose (*Colletotrichum lagenarium*), powdery mildew (*Sphaerotheca fuliginea*), gummy stem blight (*Didymella bryoniae*), Corynespora leaf spot (*Corynespora cassiicola*), Fusarium wilt (*Fusarium oxysporum*), downy mildew (*Pseudoperonospora cubensis*), Phytophthora rot (*Phytophthora capsici*), damping-off (*Pythium* sp.);

Tomato diseases: early blight (*Alternaria solani*), leaf mold (*Cladosporium fulvum*), Cercospora leaf mold (*Pseudocercospora fuligena*), late blight (*Phytophthora infestans*), powdery mildew (*Leveillula taurica*);

Eggplant diseases: brown spot (*Phomopsis vexans*), powdery mildew (*Erysiphe cichoracearum*);

Cruciferous vegetables diseases: Alternaria leaf spot (*Alternaria japonica*), white spot (*Cercosporella brassicae*), clubroot (*Plasmodiophora brassicae*), downy mildew (*Peronospora parasitica*), white rust (*Albugo candida*);

Welsh onion diseases: rust (*Puccinia allii*);

Soybean diseases: purple stain (*Cercospora kikuchii*), Sphaceloma scad (*Elsinoe glycines*), pod and stem blight (*Diaporthe phaseolorum* var. *sojae*), rust (*Phakopsora pachyrhizi*), target spot (*Corynespora cassiicola*), anthracnose (*Colletotrichum glycines, Colletotrichum truncatum*), Rhizoctonia rot (*Rhizoctonia solani*), septoria brown spot (*Septoria glycines*), Cercospora leaf spot (*Cercospora sojina*), stem rot (*Sclerotinia sclerotiorum*), powdery mildew (*Microsphaera diffusa*), Phytophthora stem and root rot (*Phytophthora sojae*), downy mildew (*Peronospora manshurica*), sudden death syndrome (*Fusarium virguliforme*), red crown rot (*Calonectria ilicicola*), Diaporthe/Phomopsis complex (*Diaporthe longicolla*);

Kidney bean diseases: stem rot (*Sclerotinia sclerotiorum*), rust (*Uromyces appendiculatus*), angular leaf spot (*Phaeoisariopsis griseola*), anthracnose (*Colletotrichum lindemuthianum*), root rot (*Fusarium solani*);

Peanut diseases: leaf spot (*Cercospora personata*), brown leaf spot (*Cercospora arachidicola*), southern blight (*Sclerotium rolfsii*), Cylindrocladium black rot (*Calonectria ilicicola*);

Garden pea diseases: powdery mildew (*Erysiphe pisi*), root rot (*Fusarium solani*);

Potato diseases: early blight (*Alternaria solani*), late blight (*Phytophthora infestans*), pink rot (*Phytophthora erythroseptica*), powdery scab (*Spongospora subterranea* f. sp. *subterranea*), Verticillium wilt (*Verticillium albo-atrum, Verticillium dahliae, Verticillium nigrescens*), dry rot (*Fusarium solani*), potato wart (*Synchytrium endobioticum*);

Strawberry diseases: powdery mildew (*Sphaerotheca humuli*);

Tea diseases: net blister blight (*Exobasidium reticulatum*), white scab (*Elsinoe leucospila*), gray blight (*Pestalotiopsis* sp.), anthracnose (*Colletotrichum theae-sinensis*);

Tobacco diseases: brown spot (*Alternaria longipes*), anthracnose (*Colletotrichum tabacum*), blue mold (*Peronospora tabacina*), black shank (*Phytophthora nicotianae*);

Sugar beet diseases: Cercospora leaf spot (*Cercospora beticola*), leaf blight (*Thanatephorus cucumeris*), root rot (*Thanatephorus cucumeris*), Aphanomyces root rot (*Aphanomyces cochlioides*), rust (*Uromyces betae*);

Rose diseases: black spot (*Diplocarpon rosae*), powdery mildew (*Sphaerotheca pannosa*);

Chrysanthemum diseases: leaf blight (*Septoria chrysanthemi-indici*), white rust (*Puccinia horiana*);

Onion diseases: Botrytis leaf blight (*Botrytis cinerea, Botrytis byssoidea, Botrytis squamosa*), gray-mold neck rot (*Botrytis allii*), small sclerotial neck rot (*Botrytis squamosa*);

Various plants diseases: Botrytis rot (*Botrytis cinerea*), Sclerotinia rot (*Sclerotinia sclerotiorum*), seedling blight (*Pythium aphanidermatum, Pythium irregulare, Pythium ultimum*).

Examples of the method for controlling a plant disease of the present invention includes an application to a plant body such as foliar application or seed disinfection; an application to a cultivation area of plant such as a soil treatment; and the like.

The amount of Compound A or the alkali metal salt thereof to be applied is usually 1 to 10000 g per 1000 m$^2$. When Compound A or the alkali metal salt thereof is formulated to an emulsion, a wettable powder, a flowable formulation or the like, it is usually diluted with water so as to have a concentration of active ingredient of 0.01 to 10000 ppm and applied, and a granule, a powder or the like is usually applied as it is.

The composition of the present invention can be used as a control agent for plant diseases in croplands such as fields, paddy fields, grasses, and orchards.

EXAMPLES

Production examples of Compound A or an alkali metal salt thereof are shown.

Compound B can be produced by the method described in EXAMPLES 4 of WO 2007/083090.

Production Example 1

70.7 g of a 27% aqueous sodium hydroxide solution was added to 488.04 g (concentration: 24.45% by weight) of a xylene solution of Compound B at 40° C., and the mixture was stirred at 40° C. for 3 hours. 300 g of water was added to the obtained mixture, and extraction was conducted. 21.9 g of 98% sulfuric acid was added dropwise to the obtained aqueous layer. The precipitated solid was filtered and dried to obtain 112.24 g of Compound A (purity: 97.9% (LC internal standard method)). The melting point of this compound was 195.2° C.

$^1$H-NMR data of Compound A is shown below.

$^1$H-NMR (DMSO-d$_6$) δ (ppm): 12.85 (1H, s), 7.94 (1H, dd), 7.61 (1H, dd), 7.31 (1H, dd), 7.20 (1H, td), 7.04 (1H, t), 7.02 (1H, dd), 4.87 (2H, s).

Production Example 2

An 8 N aqueous sodium hydroxide solution was added to a mixture of 9.95 g of Compound A and 48.55 g of ion-exchanged water so that the pH was 7.1. The resulting mixture was concentrated under reduced pressure to obtain 10.82 g of sodium salt monohydrate of Compound A. The melting point of this compound was 107.6° C.

Next, test examples are shown. A non-treated in Test Example 1 means a section in which the same operation as in a treated section is performed except that Compound A is not used.

Test Example 1

After dispensing 1 μL of a dimethyl sulfoxide solution containing a predetermined concentration of Compound A into wells of a titer plate (96 wells), 150 μL of a potato dextrose broth containing zoospores of *Phytophthora capsici* was dispensed, and the mixture was prepared so as to have a final concentration of Compound A of 100 ppm and defined as a treated section. In addition, a non-treated section was prepared in other wells. The plate was cultured at 27° C. for 3 days to proliferate *Phytophthora capsici* of the Cucurbitaceae, and then the absorbance at 600 nm of each well of the titer plate was measured and defined as the growth degree of *Phytophthora capsici*. Based on the growth degree, the efficacy was calculated using "Formula 1".

$$\text{Efficacy}(\%) = 100 \times (X-Y)/X \quad \text{"Formula 1"}$$

X: Growth degree of bacteria in non-treated section
Y: Growth degree of bacteria in treated section
As a result, the efficacy was 100%.

Test Example 2

A test was performed according to Test Example 1 using sodium salt monohydrate of Compound A in place of Compound A. As a result, the efficacy was 90%.

Comparative Test Example 1

A test was performed according to Test Example 1 using Compound B in place of Compound A. As a result, the efficacy was 64%.

INDUSTRIAL APPLICABILITY

Compound A or an alkali metal salt thereof exhibits an excellent control effect on plant diseases.

The invention claimed is:
1. 2-{[3-(2-Chloro-4-fluorophenoxy)pyridin-2-yl]oxy}acetic acid or an alkali metal salt thereof.
2. A composition comprising the compound according to claim 1 or the alkali metal salt thereof and an inert carrier.
3. A method for controlling a fungal plant disease by treating a plant or soil with an effective amount of the compound according to claim 1 or the alkali metal salt thereof.

* * * * *